(12) United States Patent
Toguchida et al.

(10) Patent No.: US 8,697,430 B2
(45) Date of Patent: Apr. 15, 2014

(54) TISSUE-DERIVED BIOMATERIAL CARRIER DEVICE

(75) Inventors: Jyuna Toguchida, Kyoto (JP); Tomoki Aoyama, Kyoto (JP); Kazuo Umihira, Kyoto (JP)

(73) Assignees: Kyoto University, Kyoto (JP); Umihira Works Co., Ltd., Kyoto (JP)

( * ) Notice: Subject to any disclaimer, the term of this patent is extended or adjusted under 35 U.S.C. 154(b) by 289 days.

(21) Appl. No.: 13/055,129

(22) PCT Filed: Jul. 23, 2009

(86) PCT No.: PCT/JP2009/003478
§ 371 (c)(1),
(2), (4) Date: Feb. 9, 2011

(87) PCT Pub. No.: WO2010/013419
PCT Pub. Date: Feb. 4, 2010

(65) Prior Publication Data
US 2011/0143425 A1  Jun. 16, 2011

(30) Foreign Application Priority Data
Jul. 29, 2008  (JP) .................................. 2008-194906

(51) Int. Cl.
*A01N 1/02* (2006.01)
*C12M 1/42* (2006.01)
*C12M 3/00* (2006.01)
*C12M 1/00* (2006.01)

(52) U.S. Cl.
CPC ............ *A01N 1/0252* (2013.01); *A01N 1/0242* (2013.01); *A01N 1/0273* (2013.01); *C12M 23/48* (2013.01); *C12M 23/52* (2013.01)
USPC ....... 435/284.1; 435/1.1; 435/1.2; 435/289.1; 435/303.1

(58) Field of Classification Search
CPC . A01N 1/0242; A01N 1/0273; A01N 1/0252; C12M 23/48; C12M 23/52; C12M 41/14; C12M 45/22
USPC .................................................. 435/1.1, 1.2
See application file for complete search history.

(56) References Cited

U.S. PATENT DOCUMENTS 6,490,880 B1 * 12/2002 Walsh ......................... 62/457.9
6,582,953 B2 * 6/2003 Brasile ....................... 435/284.1

(Continued)

FOREIGN PATENT DOCUMENTS

| JP | 07-280410 | 10/1995 |
| JP | 2003-325162 | 11/2003 |

(Continued)

OTHER PUBLICATIONS

European Application No. 09802668.5-1501 Extended European Search Report dated Nov. 8, 2013, 12 pages.

*Primary Examiner* — Nathan Bowers

(57) ABSTRACT

Disclosed is a tissue-derived biomaterial carrier device (1) comprising a carrier case 810), an arm (125) provided upright on an interior bottom wall surface of the carrier case (10), a mounting part (121), a swing mechanism (122), a temperature control box (20) provided detachably on an exterior wall surface of the carrier case (10), and a heater (201) provided in the temperature control box (20). The mounting part (121) receives the mounting of a housing vessel in which a tissue-derived biomaterial is housed (an opening part (121*a*)). The swing mechanism (122) swingably supports the mounting part (121) relative to the arm (125). With the temperature control box (20) mounted on the carrier case (10), the heater (201) in the temperature control box (20) receives the supply of electric power from a battery (203) and regulates the temperature within the carrier case (10).

20 Claims, 10 Drawing Sheets

(56) References Cited

U.S. PATENT DOCUMENTS

| | | |
|---|---|---|
| 6,881,572 B2 * | 4/2005 | Fitzgerald et al. ......... 435/303.3 |
| 2005/0153271 A1 | 7/2005 | Wenrich |
| 2005/0239190 A1 * | 10/2005 | Poo et al. .................... 435/284.1 |
| 2007/0275363 A1 * | 11/2007 | Bertram et al. ................ 435/1.2 |
| 2009/0291486 A1 * | 11/2009 | Wenrich .................... 435/284.1 |

FOREIGN PATENT DOCUMENTS

| | | |
|---|---|---|
| JP | 2004-000275 | 1/2004 |
| JP | 2004-329145 | 11/2004 |
| JP | 2005-124556 | 5/2005 |
| JP | 2007-119033 | 5/2007 |
| WO | 02/26034 | 4/2002 |

* cited by examiner

TISSUE-DERIVED BIOMATERIAL CARRIER DEVICE

RELATED APPLICATIONS

The present application claims priority from PCT/JP2009/003478 filed on Jul. 23, 2009 which claims priority from Japanese Laid Open Application 2008-194906 filed on Jul. 29, 2008.

TECHNICAL FIELD

The present invention relates to tissue-derived biomaterial carrier devices and particularly to technology for reducing the damage received by tissue-derived biomaterial during carrying.

BACKGROUND ART

In the field of regenerative medicine, research has progressed into the treatment of patients using human or animal tissue, and such treatment has to some extent become practical. For example, attempts are being made to promote tissue regeneration by taking samples of cells, blood, etc. and reintroducing the samples to the patient after growth or differentiation.

After taking samples of tissue-derived biomaterial such as cells, or after growth or differentiation, it may be necessary to carry the samples between facilities. In other words, it may be necessary to carry tissue-derived biomaterial, taken from a patient, from a hospital or other institution to a research facility for growth or differentiation. After growth or differentiation, the tissue-derived biomaterial then needs to be carried from the research facility to the hospital where the patient is located.

Devices for carrying tissue-derived biomaterial have been proposed in, for example, Patent Literatures 1, 2, and 3.

Patent Literature 1 proposes a carrier device in which a single case contains a storage compartment storing tissue-derived biomaterial therein, a temperature unit to heat or cool the storage compartment, and a control unit to control the temperature unit.

Patent Literature 2 proposes a carrier device in which a single case contains a highly antibacterial storage compartment, various gas concentration sensors, a humidifier, a heater, a temperature sensor, etc.

Finally, Patent Literature 3 proposes a carrier device in which a single case contains a storage compartment storing tissue-derived biomaterial therein, a heater, a temperature sensor, a gas concentration control unit, an ultraviolet sterilization unit, etc. Note that vibration absorbing rubber is inserted in the carrier device proposed in Patent Literature 3 before the storage compartment is installed, in order to reduce transmission of vibrations to the tissue-derived biomaterial during carrying.

CITATION LIST

Patent Literature

Patent Literature 1: Japanese Patent Application Publication No. H07-280410
Patent Literature 2: Japanese Patent Application Publication No. 2003-325162
Patent Literature 3: Japanese Patent Application Publication No. 2005-124556

SUMMARY OF INVENTION

Technical Problem

It is difficult, however, to sterilize the devices proposed in Patent Literatures 1-3 using saturated steam under pressure, since the component storing the tissue-derived biomaterial is integrated into the case with functional components, such as for adjusting temperature. Methods of sterilization include autoclave sterilization, which uses saturated steam under pressure, and gas sterilization, which uses a gas mixture of ethylene oxide (EO) and carbon dioxide ($CO_2$). In medical settings, autoclave sterilization devices are widespread, whereas few facilities have gas sterilization devices. Accordingly, only a limited number of facilities can use the devices proposed in Patent Literatures which require gas sterilization.

Furthermore, the devices proposed in Patent Literatures 1-3 cannot effectively prevent vibrations or shocks, which occur during carrying, from being transmitted to the tissue-derived biomaterial stored therein. Due to shocks or vibrations produced externally during carrying, cells or other biomaterial may collide with the inner walls of the container and become damaged. This may make the tissue-derived biomaterial unusable after carrying. Furthermore, liquid tissue-derived biomaterial, such as blood, may undergo component separation due to vibrations during carrying.

Note that while vibration absorbing rubber is used in the carrier device proposed in Patent Literature 3 in order to reduce shocks received by the tissue-derived biomaterial during carrying, almost no absorption effect is achieved when, for example, the carrier device is held firmly in hand during carrying.

In order to solve the above problems, it is an object of the present invention to provide a tissue-derived biomaterial carrier device that is suitable for sterilization that involves heating, and that controls the temperature of the contained material during carrying while effectively reducing transmission of external vibrations and shocks.

Solution to Problem

In order to fulfill the above objective, the present invention adopts the following structure.

A tissue-derived biomaterial carrier device according to the present invention comprises a carrier case, mounting part, rotation mechanism, temperature control box attachable to an exterior wall of the carrier case, and a temperature control unit disposed in the temperature control box.

The mounting part is disposed in the carrier case, and a container storing tissue-derived biomaterial is mounted into the mounting part.

The rotation mechanism swingably supports the mounting part relative to an inner wall of the carrier case.

The temperature control unit controls the temperature in the carrier case when the temperature control box is attached to the carrier case. The temperature control unit controls the temperature in the carrier case by transferring heat through the exterior wall of the carrier case to which the temperature control box is attached.

Advantageous Effects of Invention

In the tissue-derived biomaterial carrier device according to the present invention, the carrier case that contains tissue-derived biomaterial is separate from the temperature control box that includes the temperature control unit. Accordingly, with the tissue-derived biomaterial carrier device according to the present invention, before storing tissue-derived biomaterial such as cells in the carrier case, the carrier case alone can be sterilized by a means that involves heating, such as an autoclave. After storing tissue-derived biomaterial in the carrier case, the temperature control box is then mounted on the carrier case. As a result, with the tissue-derived biomaterial carrier device according to the present invention, the carrier case that stores the tissue-derived biomaterial can be sterilized by means that involves heating, such as an autoclave or dry heat sterilization, which are widespread in medical settings. Use of the tissue-derived biomaterial carrier device according to the present invention is therefore not limited to certain facilities.

In the tissue-derived biomaterial carrier device according to the present invention, after the mounting part in the carrier case receives the container containing the tissue-derived biomaterial, the temperature control box is mounted on the carrier case. The temperature of the tissue-derived biomaterial is thus appropriately maintained during carrying.

Furthermore, in the tissue-derived biomaterial carrier device according to the present invention, the container containing the tissue-derived biomaterial is swingably supported by movement of the rotation mechanism relative to the inner wall of the carrier case. Therefore, a rotational force on the mounting part produced by vibrations or shocks received by the carrier case during carrying is lessened by swinging of the rotation mechanism even when a person carries the tissue-derived biomaterial carrier device according to the present invention in hand. Accordingly, when carried, the tissue-derived biomaterial carrier device according to the present invention effectively reduces transmission of external vibrations and shocks to the contained tissue-derived biomaterial.

As a result, the tissue-derived biomaterial carrier device according to the present invention is suitable for sterilization that involves heating and controls the temperature of the contained material during carrying while effectively reducing transmission of external vibrations and shocks.

The tissue-derived biomaterial carrier device according to the present invention may adopt the following variations.

In the tissue-derived biomaterial carrier device according to the present invention, a hole may be formed in one end face of the mounting part to receive the container, and a barycentric position of the mounting part may be located on an opposite side, relative to an opening of the hole, of a location where a rotation shaft of the rotation mechanism supports the mounting part.

In the tissue-derived biomaterial carrier device according to the present invention, the rotation mechanism may have a plurality of rotation shafts whose axes intersect. With the above structure, forces applied to the tissue-derived biomaterial during carrying can be reduced more smoothly.

In the tissue-derived biomaterial carrier device according to the present invention, at least one of the rotation shafts may have a rotary damper attached thereon.

The tissue-derived biomaterial carrier device according to the present invention may further comprise an arm extending into the carrier case from the inner wall thereof; and a damper inserted between the inner wall of the carrier case and the arm, wherein the mounting part is swingably supported by the rotation mechanism relative to the arm.

The tissue-derived biomaterial carrier device according to the present invention may further comprise a sensor provided inside the carrier case and operable to measure the temperature in the carrier case, wherein the carrier case has an external connection terminal exposed on the exterior wall, and the sensor has a signal cord connecting the sensor and the external connection terminal.

In the tissue-derived biomaterial carrier device according to the present invention, a housing of the carrier case may be formed from stainless steel plate, and the sensor and the external connection terminal may be resistant to a temperature of at least 200° C.

In the tissue-derived biomaterial carrier device according to the present invention, the temperature control box may include: a terminal connectable to the external connection terminal exposed on the exterior wall of the carrier case; a controller operable to perform calculations on the temperature inside the carrier case measured by the sensor; and a power supply unit operable to supply power to the controller and the temperature control unit, and the temperature control unit may receive power from the power supply unit when the temperature control box has been attached to the carrier case and control the temperature inside the carrier case in accordance with a signal from the controller.

In the tissue-derived biomaterial carrier device according to the present invention, the power supply unit may include a battery, and the battery may be removable from the temperature control box.

In the tissue-derived biomaterial carrier device according to the present invention, the power supply unit may include a power line for receiving power from an external source.

In the tissue-derived biomaterial carrier device according to the present invention, the temperature control unit may include a heater for heating the tissue-derived biomaterial when the temperature control box has been attached to the carrier case.

In the tissue-derived biomaterial carrier device according to the present invention, the temperature control unit may include a cooling unit for cooling the tissue-derived biomaterial when the temperature control box has been attached to the carrier case. When the tissue-derived biomaterial is assumed to be film-shaped, then in the tissue-derived biomaterial carrier device according to the present invention, the edges of the tissue-derived biomaterial may be caused to bend towards the top of the container by cooling the tissue-derived biomaterial with the cooling unit. This enables the film-shaped tissue-derived biomaterial to be removed from the container while reducing damage to the tissue-derived biomaterial.

In the tissue-derived biomaterial carrier device according to the present invention, the temperature control unit may include a Peltier element.

DESCRIPTION OF EMBODIMENTS

The following examples illustrate preferred embodiments of the present invention. Note that the embodiments in the following description are merely examples used to clearly illustrate the structure, operations, and effects of the present invention. Apart from essential features, the present invention is in no way limited to the following embodiments.

Embodiment 1

1. Overall Structure of Carrier Device 1

The overall structure of a carrier device 1 for tissue-derived biomaterial according to Embodiment 1 is described with reference to FIG. 1.

Figure 1:
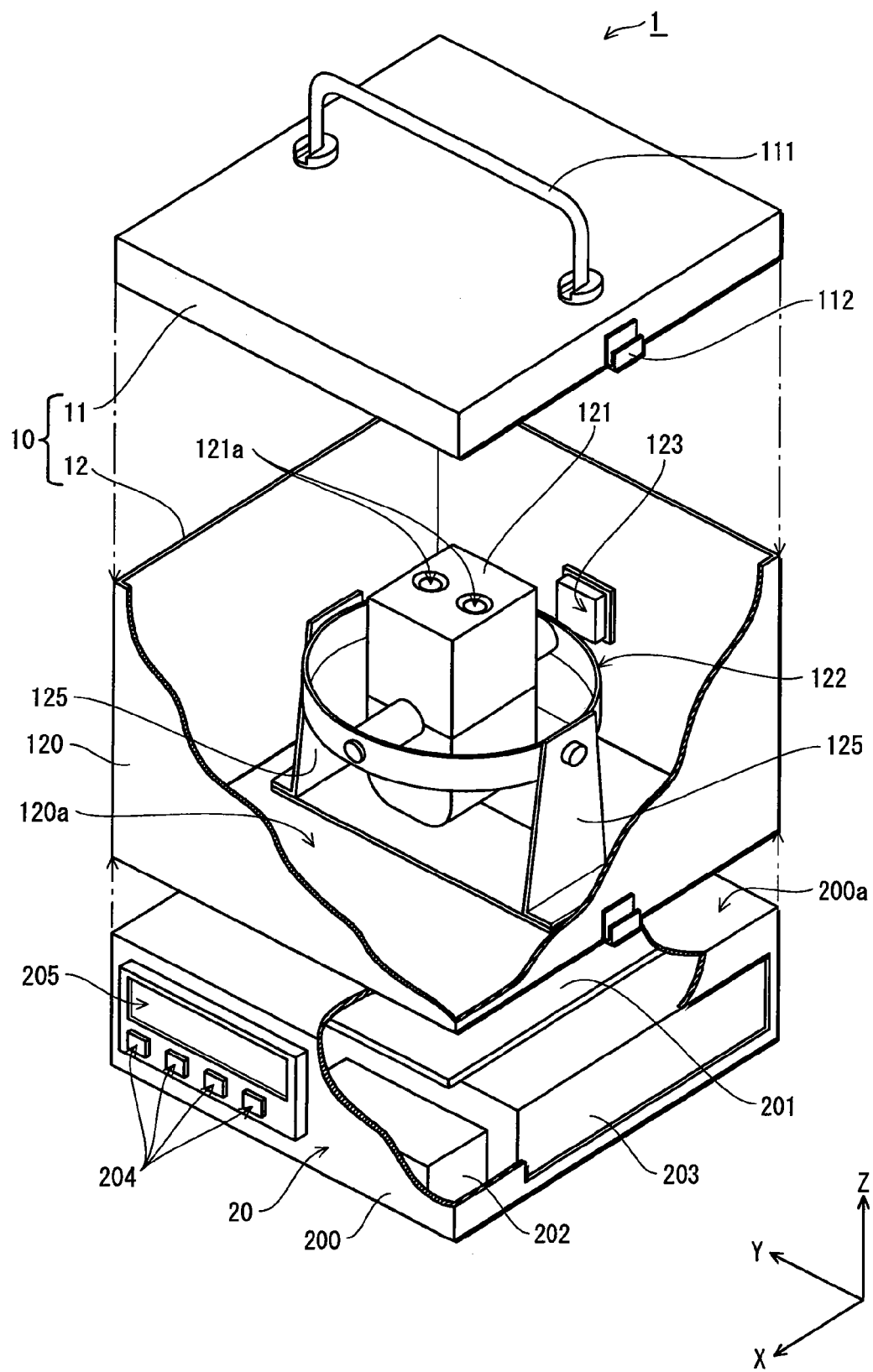
FIG. 1 is a perspective view (partially cut-out as a cross-section diagram) showing a structure of a carrier device 1 according to Embodiment 1.

As shown in FIG. 1, the main components of the carrier device 1 according to Embodiment 1 are a carrier case 10 and a temperature control box 20. The carrier case 10 and the temperature control box 20 can be attached to one another by a buckle (not shown in the figures) provided on an exterior surface of both components.

The carrier case 10 includes a lower case 12 and a top cover 11. The lower case 12 is a box in the shape of a rectangular solid having an opening at an upper end thereof along the Z axis. The top cover 11 covers the opening of a housing 120 in the lower case 12. Attaching the top cover 11 to the lower case 12 hermetically seals the carrier case 10. The housing 120 in the lower case 12 is formed from, for example, stainless steel plate.

Note that the top cover 11 is attached to the lower case 12 by a hook 112 provided on an exterior surface of the top cover 11 and by a corresponding buckle (not shown in the figures) provided on an exterior surface of the housing 120 in the lower case 12. A handle 111 for carrying is provided on the top cover 11.

A mounting part 121 is contained in the housing 120 in the lower case 12. Mounting holes 121a into which containers (omitted from FIG. 1) are mounted are provided on the upper end, along the Z axis, of the mounting part 121. The containers contain tissue-derived biomaterial. The mounting part 121 is supported by a rotation mechanism 122 relative to arms 125 provided on a bottom inner surface 120a of the housing 120 in the lower case 12.

As shown in FIG. 1, the rotation mechanism 122 is axially supported in the direction of the Y axis by the arms 125, while the rotation mechanism 122 axially supports the mounting part 121 in the direction of the X axis.

A temperature sensor 123 is provided in the housing 120 in the lower case 12 for sensing the temperature in the housing 120. The temperature sensor 123 is connected to a connector 124 (see FIG. 3) provided in an exposed state along an exterior surface of the lower case 12. Note that the temperature sensor 123, connector 124 (see FIG. 3), etc. have heat resistance to withstand temperatures of at least 200° C. The mounting part 121, rotation mechanism 122, etc. also have similar heat resistance.

The temperature control box 20 includes a housing 200 that is a smaller size, in the direction of the Z axis, than the carrier case 10. A planar heater 201, controller 202, and battery 203 are contained inside the housing 200. Among these components, the heater 201 is tightly attached to an upper surface 200a in the housing 200. When the temperature control box 20 is mounted on the carrier case 10, the heater 201 receives supply of electric power from the battery 203 and controls the temperature inside the carrier case 10.

An operation unit (switches) 204 and monitor 205 are provided on an exterior surface of the housing 200 in the temperature control box 20, on the left-hand side of the housing 200 along the X axis. The operation unit 204 is used to input temperature settings into the controller 202. The monitor 205 displays the current temperature setting, the inside temperature detected by the temperature sensor 123, the remaining capacity of the battery 203, etc.

Note that a signal cord extends from the controller 202 in the temperature control box 20, with a connector 206 (see FIG. 3) provided at the end. The connector 206 can be connected to the connector 124 (see FIG. 3) provided in the lower case 12 in the carrier case 10. The controller 202 acquires temperature information regarding the inside of the carrier case 10 through the signal cord.

2. Structure of Mounting Part 121

Figure 2:
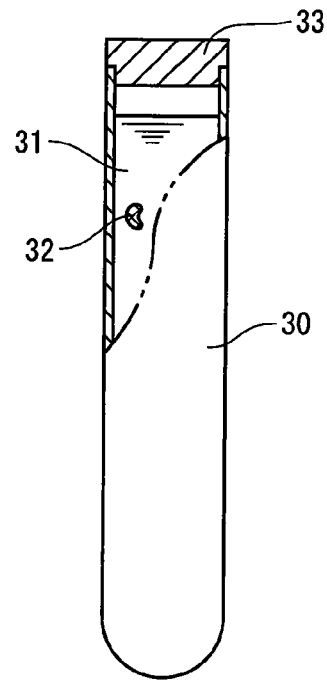
FIG. 2 is a schematic cross-section diagram showing a structure of a mounting part 121 provided in the carrier device 1.
Figure 2:
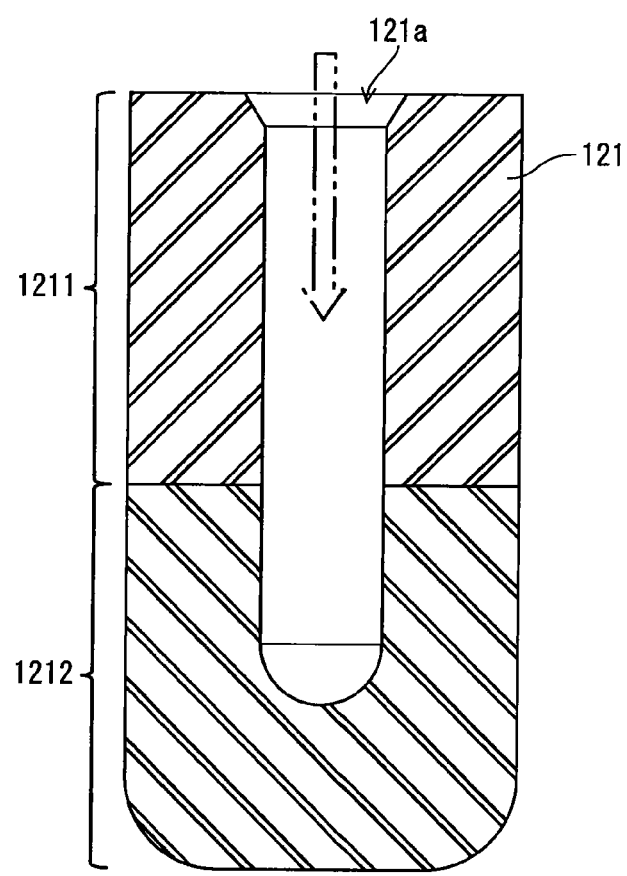

The structure of the mounting part 121 in the carrier device 1 is described with reference to FIG. 2. FIG. 2 is a cross-section diagram of the mounting part 121 and a side view (partially cut-out as a cross-section diagram) of a container 30 mounted in the mounting part 121.

As shown in FIG. 2, the mounting part 121 is provided with the mounting hole 121, which is shaped to match the size of the container 30. In a direction of depth of the mounting hole 121a, the mounting part 121 has two parts 1211 and 1212 that are made of different material and are attached to each other. The part 1211 forms the upper half of the mounting part 121, so as to encompass the opening of the mounting hole 121a into which the container 30 is inserted, and is formed from a resin material (such as polypropylene). The part 1212 forms the rest of the mounting part 121 and is formed from a metal material such as an aluminum alloy. Note that the location axially supported by the rotation mechanism 122 is the border between the part 1211 and the part 1212, or a location near this border (omitted from the figures).

By adopting the above structure in which the two parts 1211 and 1212 are connected, the barycentric position of the mounting part 121 is shifted from the location axially supported by the rotation mechanism 122 towards the part 1212. This stabilizes the position of the mounting part 121 while the rotation mechanism 122 is swinging during carrying.

The container 30 is a closed-bottom cylinder. The opening of the container 30 is sealed by a cap 33. The container 30 contains, for example, cells 32 as an example of tissue-derived biomaterial along with preservation solution 31.

3. Functional Structure of Temperature Control in Carrier Device 1

Figure 3:
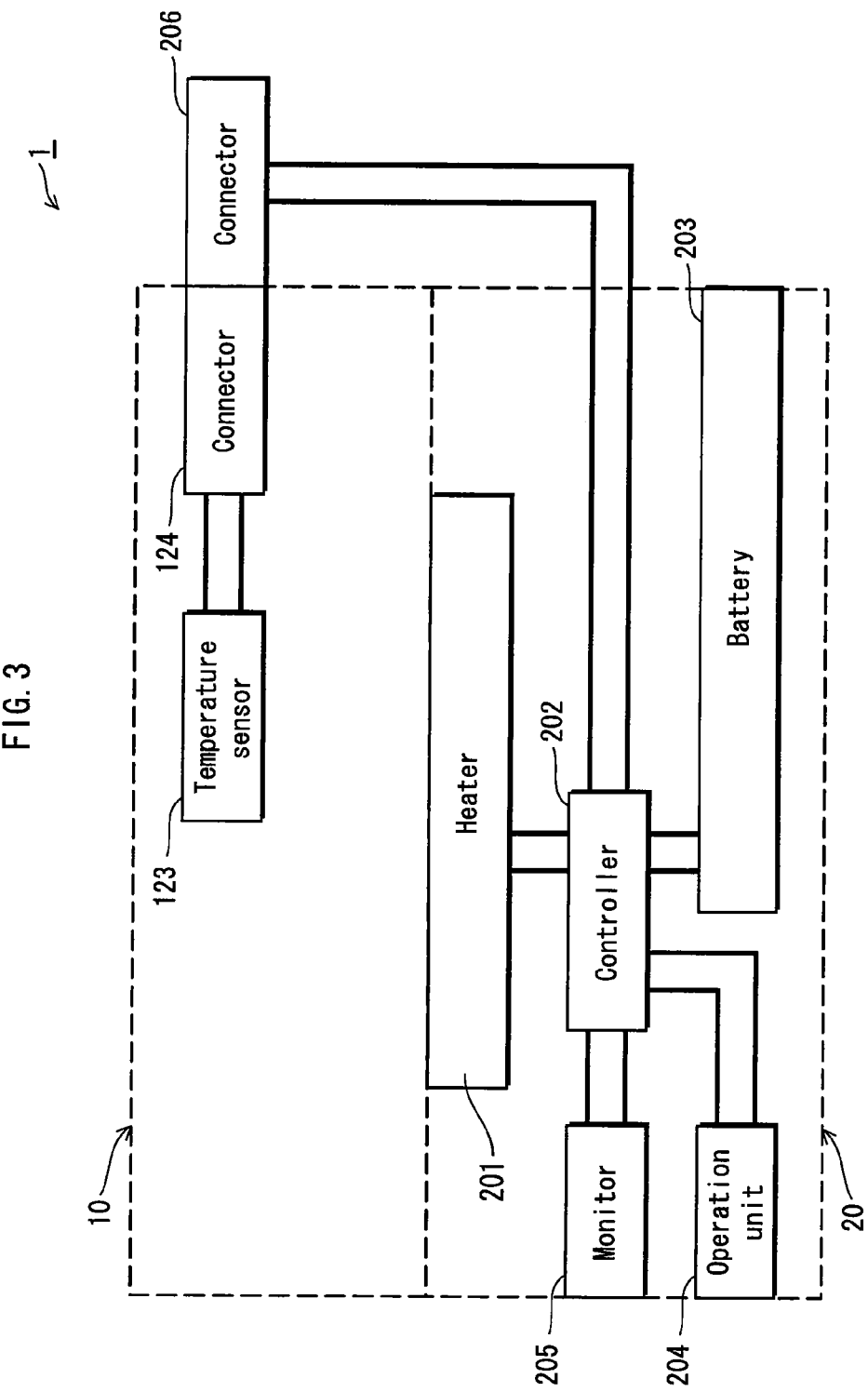
FIG. 3 is a schematic block diagram showing a structure of a temperature control system in the carrier device 1.

The functional structure of temperature control in the carrier device 1 is described with reference to FIG. 3. FIG. 3 is a schematic block diagram schematically showing a functional structure of temperature control in the carrier device 1 according to Embodiment 1.

As shown in FIG. 3, the above-described temperature sensor 123 is provided in the carrier case 10 and connected to the connector 124. The temperature sensor 123 detects the temperature inside the carrier case 10.

The heater 201, controller 202, battery 203, operation unit (switches) 204, monitor 205, etc. are provided in the temperature control box 20. In the temperature control box 20, the signal cord extends from the controller 202, with a connector 206 provided at the end. The connector 206 is connected to the connector 124 when the temperature control box 20 is mounted on the carrier case 10. Via this connection, temperature information detected by the temperature sensor 123 is input into the controller 202.

In the carrier device 1, information on temperature settings is input into the controller 202 from a user via the operation unit 204. The controller 202 controls the supply of electric power from the battery 203 and refers to temperature information from the temperature sensor 123 to control heating by the heater 201. The controller 202 also displays, on the monitor 205, the temperature information detected by the temperature sensor 123, information on temperature settings, information on the remaining capacity of the battery 203, etc.

4. Temperature Control by the Controller 202

Next, temperature control by the controller 202 in the carrier device 1 is described with reference to FIG. 4.

Figure 4:
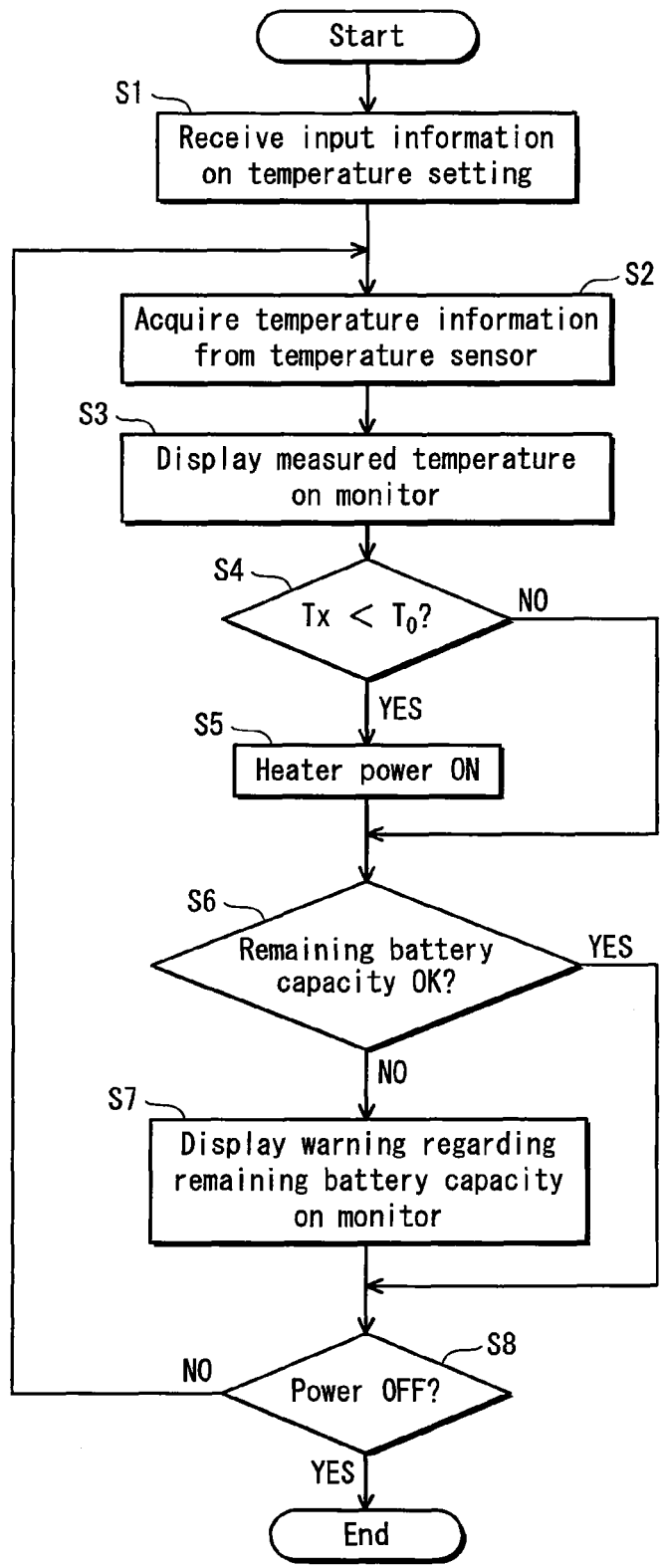
FIG. 4 is an operational flowchart showing temperature control performed by a controller 202.

As shown in FIG. 4, the controller 202 receives input of information on temperature settings from the user (step S1). Upon receiving input of information on temperature settings from the user, the controller 202 acquires information on measured temperature from the temperature sensor 123 (step S2), displays the acquired information on the monitor 205 (step S3), and compares the acquired temperature $T_X$ with the set temperature $T_0$ (step S4).

If the comparison indicates that $T_X < T_0$ (step S4: Yes), the controller 202 provides the heater 201 with power from the battery 203 and turns the heater 201 "ON" (step S5), thus increasing the temperature inside the carrier case 10. If the comparison indicates that $T_X \geq T_0$ (step S4: No), then power is not supplied to the heater 201 (heater 201 is turned "OFF").

In this Embodiment, in which the tissue-derived biomaterial is assumed to be cells 32, the temperature setting $T_0$ is 37° C., with an acceptable range of ±2° C.

Next, the controller 202 detects the remaining capacity of the battery 203 and determines whether the battery needs to be replaced based on a standard capacity pre-specified according to the type of the battery 203 (step S6). If the remaining capacity of the battery 203 falls below the pre-specified capacity (step S6: No), the controller 202 displays a warning regarding the remaining battery capacity on the monitor 205 to alert the user (step S7).

The controller 202 then determines whether the user has instructed to turn the power OFF (step S8). If no "power OFF" instruction has been provided, then control operations are repeated starting with step S2. When a "power OFF" signal is received, control operations terminate.

Note that with the carrier device 1 according to Embodiment 1, the battery 203 in the temperature control box 20 can be replaced even during carrying, as shown in FIG. 1. Specifically, an opening for replacing the battery 203 is provided in the housing 200 in the temperature control box 20. Furthermore, the battery 203 and the controller 202 are connected by a removable connector (not shown in the figures).

The controller 202 has a built-in backup battery so that the controller 202 can continue to operate when the remaining capacity of the battery 203 is lower than the specified capacity and while the user is replacing the battery 203.

5. Advantages of the Carrier Device 1

In the carrier device 1 according to Embodiment 1, the carrier case 10 which contains tissue-derived biomaterial is separate from the temperature control box 20, which includes the temperature control unit (heater 201, controller 202, battery 203, etc.). Therefore, before storing tissue-derived biomaterial such as the cells 32 in the carrier case 10, the carrier case 10 alone can be sterilized in an autoclave. After inserting the container 30 that contains the cells 32 into the carrier case 10, the temperature control box 20 is then mounted on the carrier case 10. Sterilization in the autoclave is performed at, for example, twice atmospheric pressure at a temperature of 121° C. for 15-20 minutes with the carrier case 10 inserted therein. Accordingly, the carrier case 10 storing the cells 32 in the carrier device 1 can be sterilized using autoclave sterilizers that are widespread in medical settings. Facilities that can use the carrier device 1 are therefore not limited.

Since the housing 120 in the lower case 12 of the carrier case 10 is formed from stainless steel plate, and since the temperature sensor 123 and connector 124 are resistant to at least a temperature of 200° C., the carrier case 10 can easily withstand the heat of sterilization in an autoclave. Among the components in the mounting part 121, the part 1211 is made from resin material. However, resin material that can resist relatively high temperatures, such as polypropylene, is used. The part 1211 is thus sufficiently compatible with the heat from the autoclave.

Furthermore, the temperature of the cells 32 can be appropriately managed while the carrier device 1 is being carried. This is because the temperature control box 20 is mounted on the carrier case 10 after the container 30 containing the cells 32 is inserted into the mounting part 121 in the carrier case 10.

In the carrier device 1, the container 30 containing the cells 32 is swingably supported by the rotation mechanism 122 relative to the arms 125 that are provided upright on the bottom inner surface 120a of the lower case 12 in the carrier case 10. Therefore, vibrations or shocks are lessened by swinging of the rotation mechanism 122 even when the user carries the carrier device 1 in hand. Accordingly, when carried, the carrier device 1 effectively reduces transmission of external vibrations and shocks to the cells 32 stored in the container 30.

Note that, as shown in FIG. 1, the rotation mechanism 122 in the carrier device 1 according to Embodiment 1 has rotation shafts along two axes. Therefore, the carrier device 1 effectively reduces damage to the cells 32 by vibrations in the X-Z plane, vibrations in the Y-Z plane, and vibrations that are a combination thereof.

In the carrier device 1 according to Embodiment 1, the mounting part 121 is formed by a combination of two parts, 1211 and 1212. These two parts 1211 and 1212 are formed from different material so that the barycentric position exists at a position lower than the axial support by the rotation mechanism 122. Accordingly, the position of the mounting part 121, into which the container 30 is mounted, is stable.

Furthermore, in the carrier device 1, the heater 201 in the temperature control box 20 is driven by power supplied from the battery 203. Therefore, the path over which the carrier device 1 is carried is not limited with respect to a power source. As shown in FIG. 1, the battery 203 in the temperature control box 20 of the carrier device 1 can be replaced. Therefore, even if the remaining capacity of the battery 203 becomes low during carrying, the temperature is stably controlled by replacing the battery 203.

Embodiment 2

The structure of a carrier device 2 according to Embodiment 2 is now described with reference to FIGS. 5 and 6.

1. Structure of Mounting Part 421

First, the structure of a mounting part 421, which differs from the carrier device 1 according to Embodiment 1, is described with reference to FIG. 5. FIG. 5 shows the mounting part 421 as supported by arms 425 via a rotation mechanism 422.

Figure 5:
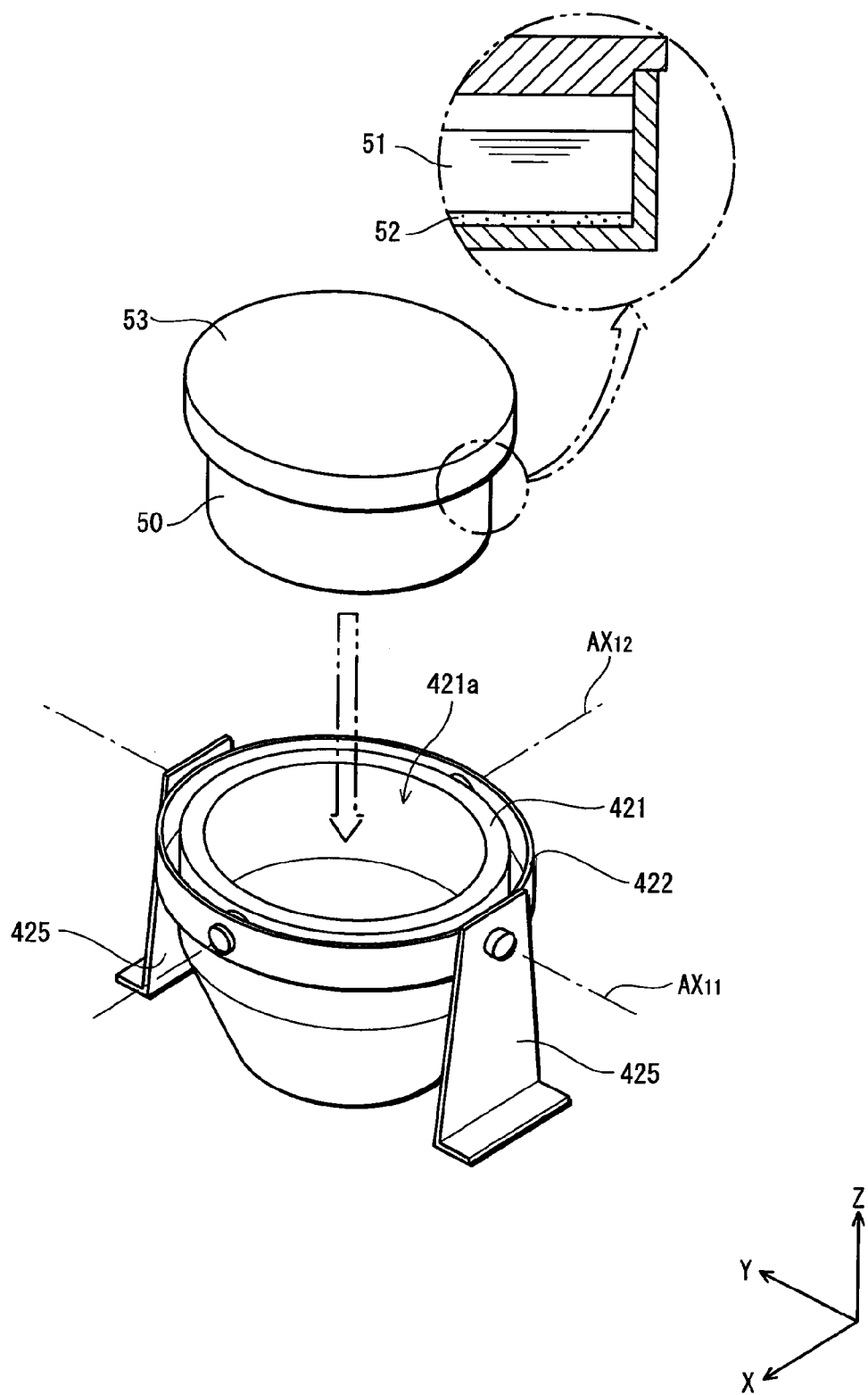
FIG. 5 is a schematic cross-section diagram showing a structure of a mounting part 421 provided in a carrier device according to Embodiment 2.

As shown in FIG. 5, the carrier device 2 according to Embodiment 2 is for carrying a film-shaped cell sheet 52. A container 50 that is mounted on the carrier device 2 is thus shaped as a shallow dish, and a cap 53 is accordingly a larger size. The cell sheet 52 is stuck to the bottom of the container 50, and the container 50 is filled with preservation solution 51 above the cell sheet 52.

The mounting part 421 according to Embodiment 2 has a containment hole 421a whose shape matches the container 50. The mounting part 421 is swingably supported by the rotation mechanism 422 relative to the arms 425 that are provided upright on a bottom inner surface of the lower case. In Embodiment 2 as well, the rotation mechanism 422 has rotation shafts along two axes, $AX_{11}$ and $AX_{12}$.

The cross-sectional size of the opening in the mounting hole 421a in the mounting part 421 is set to be approximately the same as the outer size of the container 50. When mounted in the mounting hole 421a, the container 50 thus does not wobble in the X-Y directions. The same is true for the mounting hole 121a in the mounting part 121 and the container 30 in Embodiment 1.

In the carrier device 2 according to Embodiment 2, the structure of each component in the carrier case apart from the mounting part 421 is the same as the carrier case 10 in the carrier device 1 according to Embodiment 1.

2. Temperature Control

The carrying structure of the carrier device 2 according to Embodiment 2 is described with reference to FIG. 6.

(1) During Carrying

As with the carrier device 1 according to Embodiment 1, the temperature control box 20 with the built-in heater 201 is mounted on a carrier case 40 when the carrier device 2 according to Embodiment 2 is carried. The temperature control box is as described in Embodiment 1. The cell sheet 52 is thus maintained at an appropriate temperature during carrying of the carrier device 2 as well.

(7) After Arrival at Destination

Figure 6:
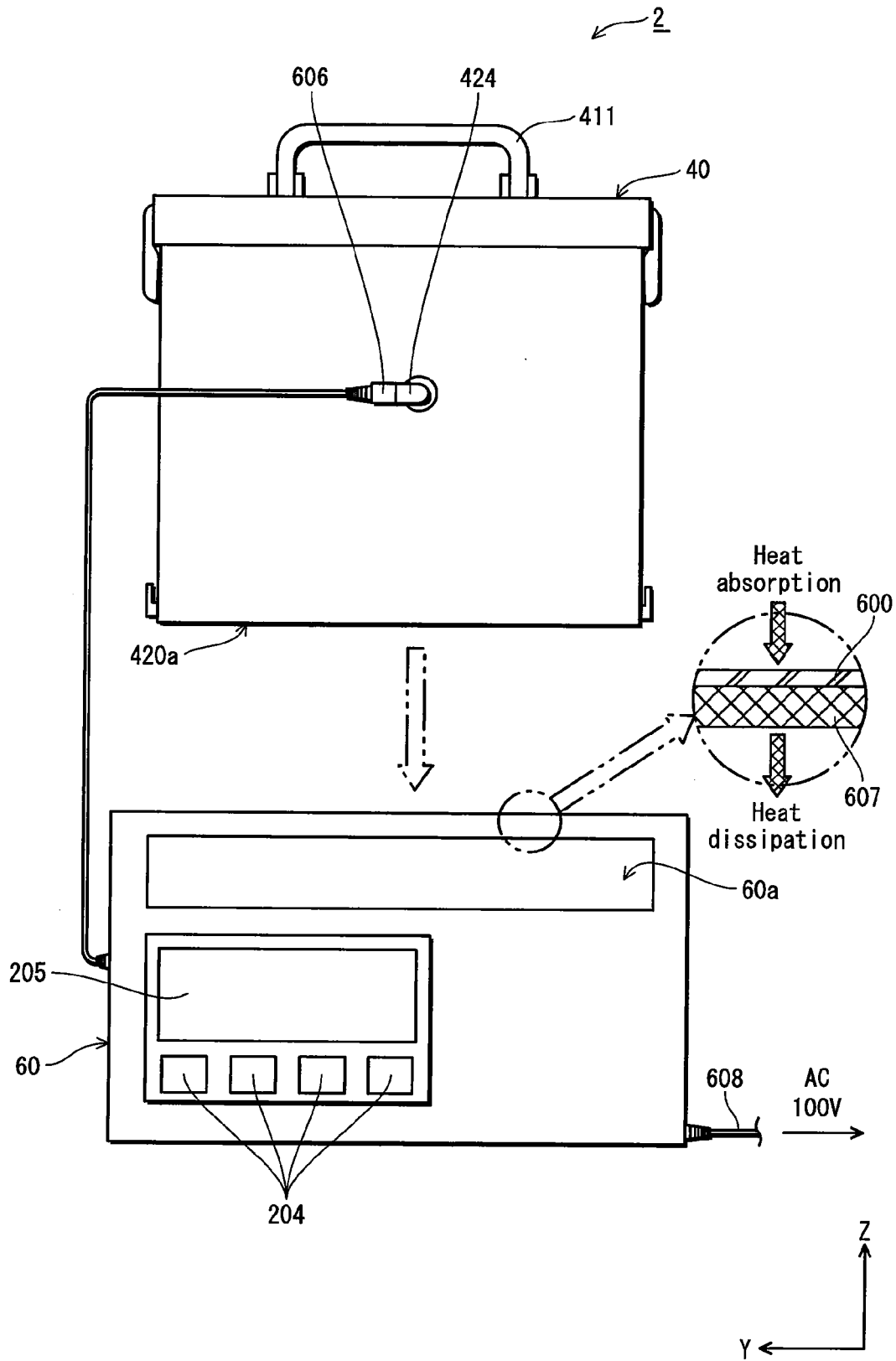
FIG. 6 is a side view showing a structure of a carrier device 2 according to Embodiment 2.

Next, as shown in FIG. 6, after arrival at the destination, the temperature control box 20 for heating that was mounted on the carrier case 40 is removed, and a temperature control box 60 for cooling is mounted on the carrier ease 40 instead. As above, when mounting the temperature control box 60 for cooling on the carrier case 40, the top of the temperature control box 60 is tightly connected to the bottom 420a of the housing in the lower case in the carrier case 40.

A Peltier element 607 is built into the temperature control box 60 as a cooling element. When the temperature control box 60 is mounted on the carrier case 40, the Peltier element 607 thermally couples with the carrier case 40 through the housing 600. The temperature control box 60 has a cavity 60a below the location where the Peltier element 607 is built in, i.e. below in the direction of the Z axis. The main surface of the heat dissipating side of the Peltier element 607 is thus outwardly exposed.

Furthermore, a power cord 608 for receiving power from a commercial power source extends from the temperature control box 60. The temperature control box 60 differs from the temperature control box 20 used during carrying in that it is assumed to be used within a facility to which the carrier case 40 has arrived. Therefore, the temperature control box 60 receives power from a commercial power source in order to efficiently lower the temperature within the carrier case 40. A regulated power supply circuit (omitted from the figures) is built into the temperature control box 60, and alternating current that is input is transformed into direct current and then supplied to the Peltier element 607.

Note that a signal cord extends from the temperature control box 60 as well, and a connector 606 provided at the end of the signal cord is connected to a connector 424 in the temperature sensor provided in the carrier case 40. The user can input a temperature setting into the operation unit 204 and confirm a variety of temperature information displayed on the monitor 205.

In the temperature control box 60 according to Embodiment 2, the cell sheet 52, which as described above is carried while being controlled at a temperature of approximately 37° C. (for example, within a range of ±2° C.), is cooled until reaching a temperature of 34° C.±2° C.

3. Changes to the Cell Sheet 52 Upon Cooling

Figure 7A:
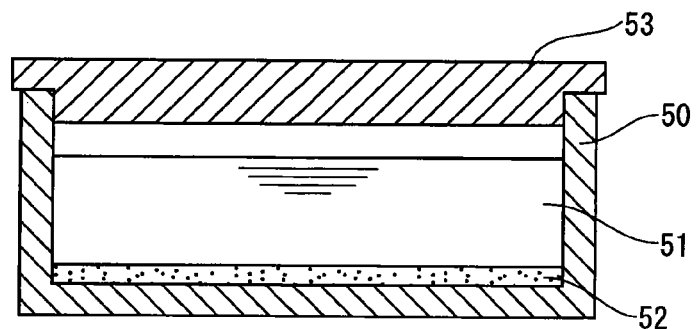
FIG. 7A is a schematic cross-section diagram showing the condition of a cell sheet 52 before cooling.
Figure 7B:
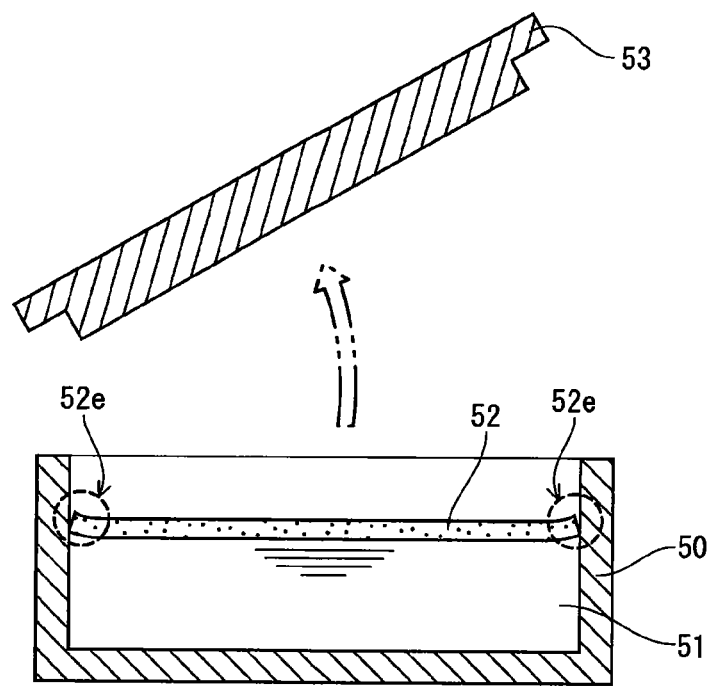
FIG. 7B is a schematic cross-section diagram showing the condition of the cell sheet 52 upon cooling.

With reference to FIGS. 7A and 7B, the following describes changes to the cell sheet 52 when cooled to 34° C.±2° C. by mounting the temperature control box 60 as described above. FIG. 7A shows the condition of the cell sheet 52 before cooling, and FIG. 7B shows the condition of the cell sheet 52 upon cooling to 34° C.±2° C.

As shown in FIG. 7A, before cooling, the cell sheet 52 is stuck to the bottom of the container 50, and the container 50 is filled with preservation solution 51 above the cell sheet 52.

On the other hand, as shown in FIG. 7B, upon cooling the cell sheet 52 in the container 50 to 34° C.±2° C., the cell sheet 52 floats to near the surface of the preservation solution 51, and the edges 52e bend upwards. The user removes the cell sheet 52 from the container 50 by the bent edges 52e. The carrier device 2 according to Embodiment 2 avoids problems such as wrinkling while allowing the cell sheet 52 to be removed from the container 50 using the edges 52e that are bent by cooling.

Embodiment 3

The structure of a carrier device 3 according to Embodiment 3 is now described with reference to FIG. 8.

Figure 8:
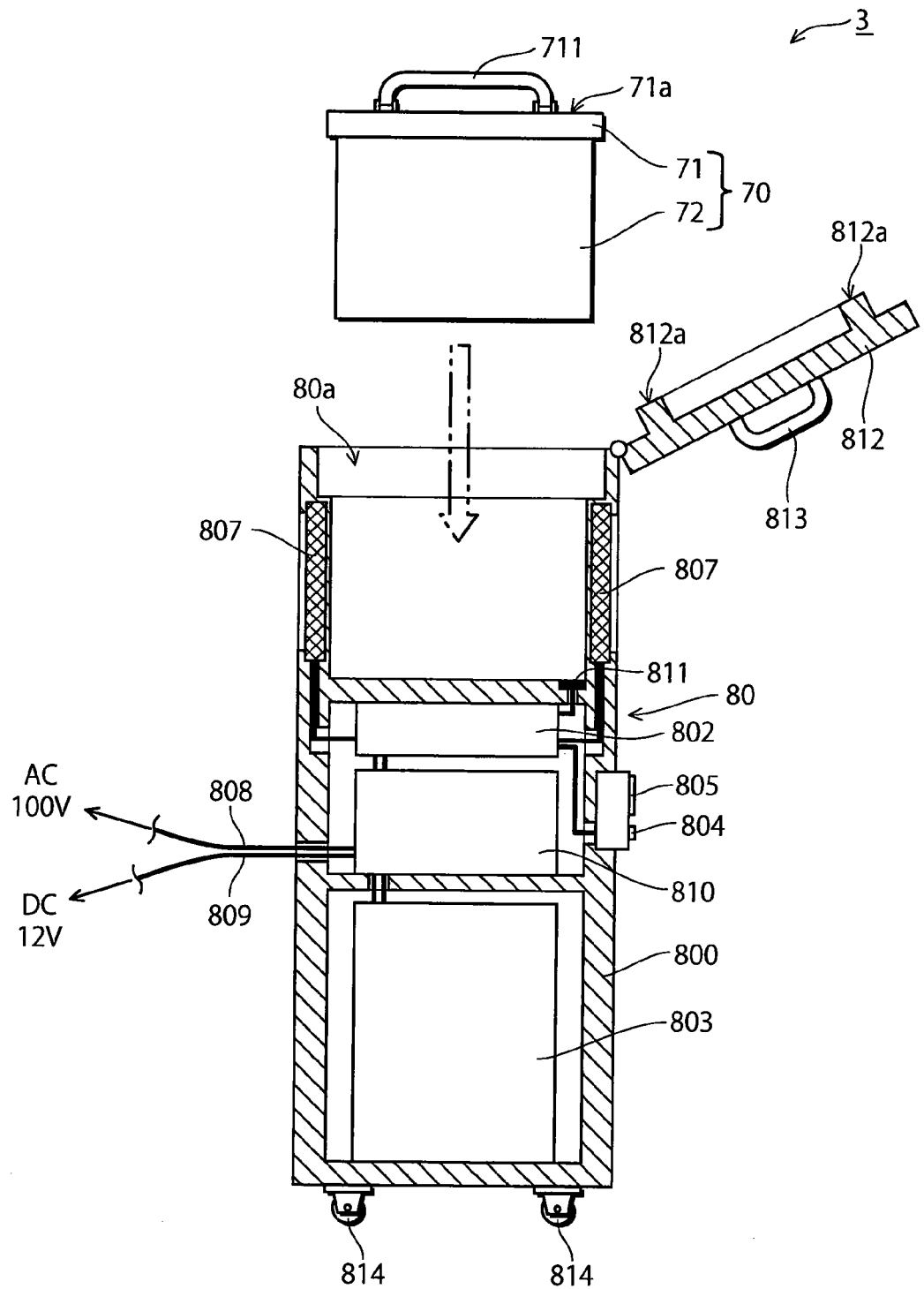
FIG. 8 is a schematic cross-section diagram showing a structure of a carrier device 3 according to Embodiment 3.

As shown in FIG. 8, the carrier device 3 according to Embodiment 3 is a combination of a carrier case 70 and a mountable temperature control box 80. The carrier case 70 has a top cover 71 and a lower case 72. A handle 711 is provided on the top cover 71 for use until the carrier case 70 is stored in a storage compartment 80a in the temperature control box 80. The housing of the carrier case 70 is formed from stainless steel plate, and the carrier case 70 houses therein similar constituent elements to Embodiments 1 and 2. However, it is assumed that the carrier device 3 according to Embodiment 3 is used to carry organs, and thus the size of the container is set accordingly. The rotation mechanism, arm, etc. are therefore larger than in Embodiments 1 and 2.

The temperature control box 80 includes a housing 800 and a lid 812. The housing 800 has an opening at the top thereof that exposes the storage compartment 80a. The lid 812 closes the opening after the carrier case 70 is stored in the storage compartment 80a. A handle 813 is provided on the lid 812 for carrying the carrier device 3. Protrusions 812a are also provided on the lid 812, facing inwards. The protrusions 812.a push down on an upper surface 71a of the top cover 71 so that the carrier case 70 stored in the storage compartment 80a does not vibrate during carrying.

Peltier elements 807 are provided in the temperature control box 80 as a cooling means, surrounding the storage compartment 80a. Each of the Peltier elements 807 is disposed so that the heat absorption side faces the storage compartment 80a, and the heat dissipating side faces the outside. Furthermore, on the bottom wall facing the storage compartment 80a, a temperature sensor 811 is provided for detecting the temperature of the housing in the carrier case 70. In the carrier device according to Embodiment 3, the temperature of the housing in the carrier case 70 is used to control the temperature in the carrier case 70.

Below the storage compartment 80a in the temperature control box 80, a controller 802, power unit 810, and battery 803 are stored in this order. The controller 802 performs the same operations as the controller 202 in the carrier device 1 according to Embodiment 1.

An operation unit 804 and monitor 805 are provided on an exterior wall of the housing 800 in the temperature control box 80. The operation unit 804 and the monitor 805 are connected to the controller 802. As in the carrier device 1 according to Embodiment 1, the user inputs information on temperature settings, etc. into the operation unit 804, and the monitor 805 displays the temperature detected by the temperature sensor 811, the temperature setting, the remaining capacity of the battery 803, etc.

Two types of power cords 808 and 809 extend from the power unit 810. A connector is provided at the end of each power cord (omitted from the figures). As shown in FIG. 8, the power cord 808 is for AC 100V power, whereas the power cord 809 is for DC 12V power. The connector for each power cord is of an appropriate shape. The power unit 810 has, built in, a part that functions as an uninterruptible power supply (UPS) and that charges the battery 803 while receiving power input of AC 100V or DC 12V. When not receiving power from an external source, the power unit 810 provides the Peltier elements 807 with power from the battery 803.

The battery 803 has a larger capacity than the battery provided in the carrier devices 1 and 2 according to Embodiments 1 and 2 respectively. An alkaline secondary battery, non-aqueous secondary battery, etc. may be used.

Four casters 814 are provided at the bottom of the housing 800 in the temperature control box 80 so that, after storing the carrier case 70 in the storage compartment 80a, the user can roll the carrier device 3 while gripping the handle 813.

It is assumed that the carrier device 3 according to Embodiment 3 is used to carry organs or the like, and therefore the organs in the carrier case 70 stored in the storage compartment 80a are maintained at a low temperature of 4° C.±2° C. In order to maintain the temperature inside the carrier case 70 in a range of 4° C.±2° C. during carrying of the carrier device 3, the heat absorption function of the Peltier elements 807 is used, for which reason the large battery 803 and the power cords 808 and 809 for drawing in external power are provided.

In the carrier device 3 with the above structure, the Peltier elements 807 are driven by receiving power through the power cords 808 and 809 in locations where such external power is available and by using the built-in battery 803 in locations where it is difficult to receive such external power. This enables the carrier device 3 to cool the carrier case 70 for an extended period of time during carrying of organs.

Note that in the carrier device 3 according to Embodiment 3 as well, while omitted from FIG. 8, a mounting part on which the container is mounted is swingably supported by a rotation mechanism relative to arms in the carrier case 70. Therefore, the carrier device 3 according to Embodiment 3 also reduces damage to the tissue-derived biomaterial, i.e. the organs or the like, due to vibrations during carrying.

[Modification 1]

Figure 9:
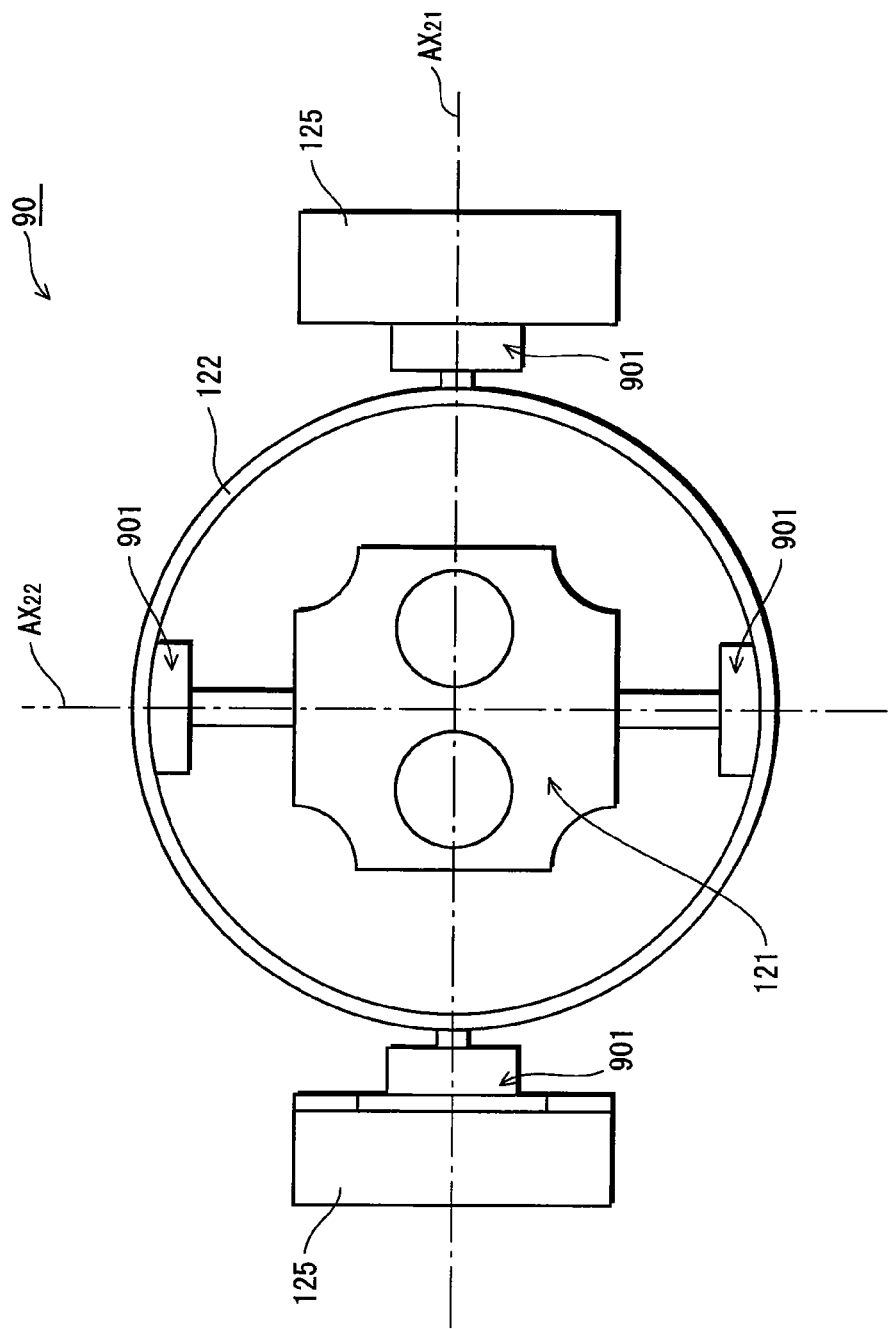
FIG. 9 is a top view showing a structure of a mounting unit 90 in a carrier device according to Modification 1.

The structure of a carrier device according to Modification 1 is described with reference to FIG. 9. FIG. 9 is a top view showing, within the structure of the carrier device, a rotation unit 90 that includes the mounting part 121, rotation mechanism 122, and arms 125. Except for the rotation unit 90, the structure of the carrier device is the same as the carrier device 1 according to Embodiment 1. Therefore, the structure is not shown in the figures, and a description thereof is omitted.

As shown in FIG. 9, between the mounting part 121 and the rotation mechanism 122, as well as between the rotation mechanism 122 and the arms 125, a rotary damper 901 is provided where each shaft is attached in the rotation unit 90 according to Modification 1.

By thus providing a rotary damper 901 where each shaft is attached in the rotation unit 90 according to Modification 1, swinging of the mounting part 121 relative to the arms 125, due to vibrations or the like that occur during carrying, is quickly diminished. In other words, swinging is lessened by insertion of the rotary dampers 901, thus further reducing damage to the tissue-derived biomaterial during carrying.

Note that the type, size, etc. of the rotary dampers 901 can be selected in accordance with the type, size, etc. of the tissue-derived biomaterial to be carried. Out of consideration for autoclave sterilization, however, the rotary dampers 901 should have resistance to temperatures of 120° C.-200° C.

[Modification 2]

Figure 10:
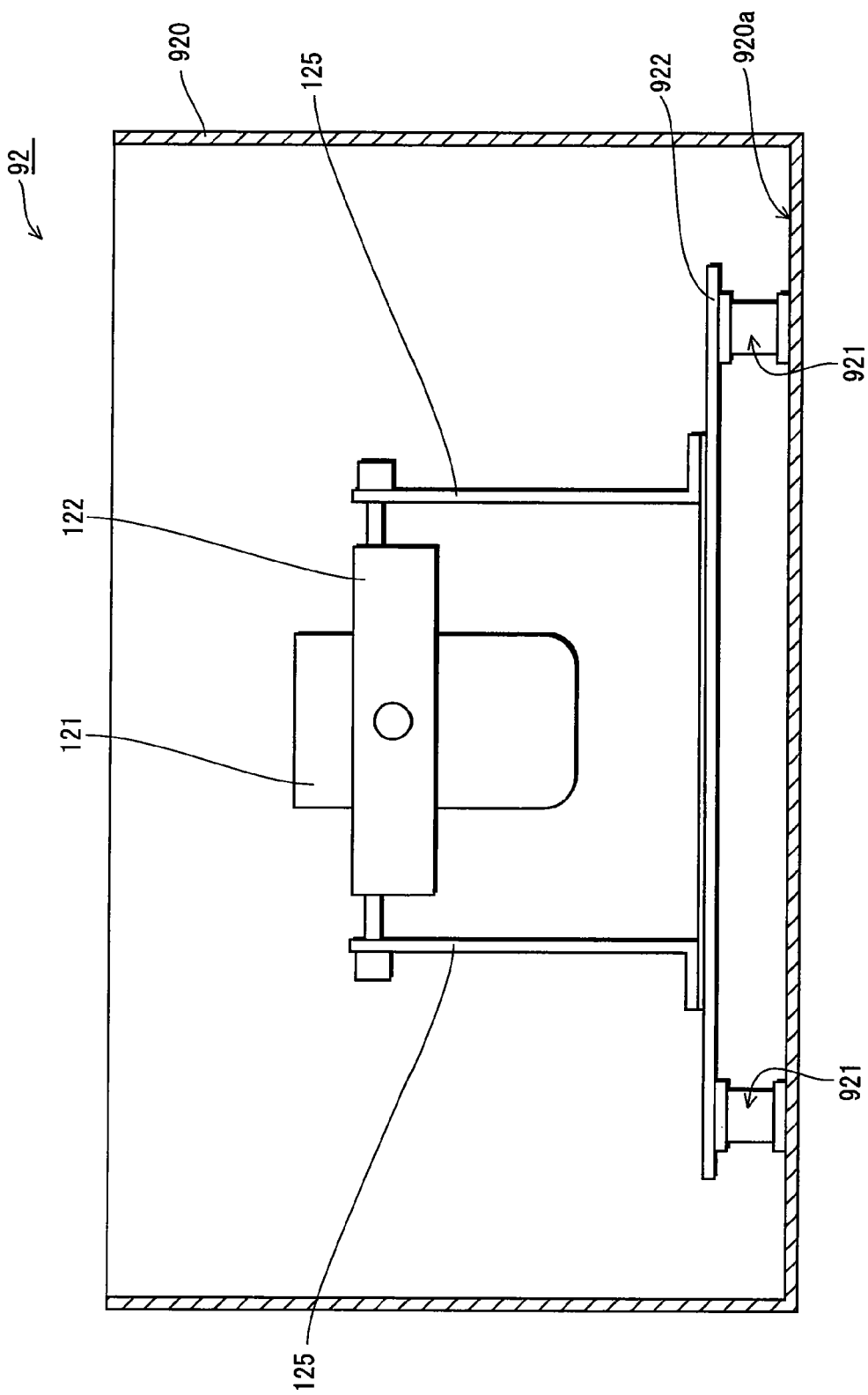
FIG. 10 is a schematic cross-section diagram showing a structure of a lower case 92 in a carrier device according to Modification 2.

The structure of a carrier device according to Modification 2 is described with reference to FIG. 10. Among the components of the carrier device, FIG. 10 is a cross-section diagram showing a structure of a lower case 92 in a carrier case. Except for the lower case 92, the structure of the carrier device is the same as the carrier device 1 according to Embodiment 1. Therefore, the structure is not shown in the figures, and a description thereof is omitted.

As shown in FIG. 10, in the lower case 92 according to Modification 2, a sub-baseboard 922 is provided, as are a plurality of dampers 921 between a bottom 920a of a housing 920 and the sub-baseboard 922. The sub-baseboard 922 is roughly parallel to the bottom 920a of the housing 920.

Two arms 125 are provided upright on the sub-baseboard 922, and the mounting part 121 is swingably supported by the rotation mechanism 122 relative to the arms 125. The mounting part 121 and the rotation mechanism 122 have the same structure as in the carrier device 1 according to Embodiment 1.

While not shown in FIG. 10, a temperature sensor is provided on an inner side wall of the housing 920 and is connected to a connector provided on an exterior side wall.

As shown in FIG. 10, in the lower case 92 in the carrier device according to Modification 2, the arms 125 are provided upright with the dampers 921 between the arms 125 and the bottom 920a of the housing 920. Therefore, during carrying of the carrier device according to Modification 2, vibrations occurring in a vertical direction are reduced by the dampers 921.

Accordingly, in addition to the advantageous effects of the carrier device 1 according to Embodiment 1, damage to the tissue-derived biomaterial due to vibrations produced by vertical motion can also be reduced in the carrier device according to Modification 2.

[Other Considerations]

As an example of tissue-derived biomaterial that is carried, cells 32 are cited in Embodiment 1, a cell sheet 52 is cited in Embodiment 2, and organs are cited in Embodiment 3. The tissue-derived biomaterial that is carried in the carrier device according to the present invention is not limited to these examples, but also includes organs, tissue, cells, blood, specific components of blood, purified protein, cultured cells, blood serum, cultured tissue, etc.

Furthermore, since cells 32 are carried in the carrier device 1 according to Embodiment 1, the temperature during carrying is 37° C., and since organs are carried in the carrier device 3 according to Embodiment 3, the temperature during carrying is 4° C.±2° C. However, the present invention is not limited to these temperatures during carrying, and the tissue-derived biomaterial that is carried can be maintained at any temperature.

In the carrier device 1 according to Embodiment 1, a heater 201 is used as a heating means, but a Peltier element may be used for heating instead. In other words, the tissue-derived biomaterial can be heated by reversing the cooling site of the Peltier element and applying current.

The carrier devices 1, 2, and 3 respectively according to Embodiments 1, 2, and 3 adopt batteries 203 and 803, which are chemical cells, as an example of a power supply, yet it is not necessary to use a chemical cell. For example, a fuel cell, electric double-layer capacitor, etc. may be used.

In the carrier device 3 according to Embodiment 3, Peltier elements 807 are used as means for cooling the carrier case 70, but any structure other than Peltier elements 807 that can be built into the housing 800 in the temperature control box 80 may be used. For example, a vapor compression cooling means, vapor absorption cooling means, etc. may be used.

In the carrier devices 1, 2, and 3 respectively according to Embodiments 1, 2, and 3, stainless steel plate is used to form the housing in the carrier cases 10, 40, and 70, yet the present invention is not limited in this way. Any material that can resist an autoclave and that can smoothly exchange heat with the temperature control boxes 20, 60, and 80 may be used. For example, steel plate provided with corrosion-resistant plating may be used.

In the carrier device 3 according to Embodiment 3, casters 814 are provided on the bottom of the housing 800 in the temperature control box 80, but instead of the casters 814, air-inflated tires may be used, and shock absorbers may be attached. When casters 814 are attached as in the carrier device 3, then in accordance with overall weight, material may be carried with motorized assistance by adding an electric motor or the like to aid in moving the carrier device.

In Embodiments 1 and 2 and Modifications 1 and 2, the rotation mechanisms 122 and 422 have two axes, but a rotation mechanism with three or more axes may be used. By supporting the mounting parts 121 and 421 with a greater number of axes, the advantageous effects are reliably achieved against vibrations from a variety of directions.

In Embodiments 1, 2, and 3, the mounting parts 121 and 421 are swingably supported by the rotation mechanisms 122 and 422 relative to the arms 125 and 425, but it is not necessary that the mounting parts 121 and 421 be swingably supported relative to the arms 125 and 425. For example, the rotation mechanisms 122 and 422 may be attached to a shaft extending inwards from the inner wall of the carrier cases 10, 40, and 70.

As shown in FIG. 4, heating by the heater 201 is controlled to be ON or OFF by the controller 202 of the carrier device 1 according to Embodiment 1, yet inverter control may be performed.

Additionally, the temperature sensor is not limited to being provided in the housing 120 of the lower cases 12 and 42 respectively in the carrier cases 10 and 40, but may for example be built into the mounting parts 121 and 421. It is necessary, however, not to obstruct swinging by the rotation mechanisms 122 and 422.

In Embodiments 1, 2, and 3 and Modifications 1 and 2, the outside of the carrier cases 10, 40, and 70 is exposed. However, when there is a large difference between the temperature setting and the outside temperature (for example, when carrying material in a cold region), the outside of the carrier cases 10, 40, and 70 may be covered with insulating material. The temperature in the carrier cases 10, 40, and 70 is thus controlled more accurately, and the amount of energy expended is reduced.

INDUSTRIAL APPLICABILITY

The present invention is useful in the field of regenerative medicine for achieving a carrier device that can carry tissue-derived biomaterial, such as cells, without damaging the biomaterial.

REFERENCE SIGNS LIST 1, 2, 3 carrier device
10, 40, 70 carrier case
11, 71 top cover
12, 72, 92 lower case
20, 60, 80 temperature control box
30, 50 container
31, 51 preservation solution
32 cells
33, 53 cap
52 cell sheet
90 mounting unit
111, 411, 711 handle
112 hook.
120, 920 housing
121, 421 mounting part.
122, 422 rotation mechanism
123, 811 temperature sensor
124, 424 connector
125, 425 arm
200, 600, 800 housing
201 heater
202, 802 controller
203, 803 battery
204, 804 operation unit
205, 805 monitor
206, 606 connector
607, 807 Peltier element
608, 808, 809 power cord
810 power unit
812 lid
813 handle
814 caster
901 rotary damper
921 damper
922 sub baseboard

The invention claimed is:

1. A tissue-derived biomaterial carrier device comprising:
a carrier unit comprising a carrier case;
a temperature control box detachable from an exterior wall of the carrier case; and
a temperature control unit disposed in the temperature control box and configured to control the temperature in the carrier case, when the temperature control box has been attached to the carrier case, by transferring heat through the exterior wall of the carrier case, wherein
the carrier unit further comprises:
   a mounting part disposed in the carrier case and configured to receive a container storing tissue-derived biomaterial; and
   a rotation mechanism disposed with respect to an inner wall of the carrier case, the rotation mechanism having at least two rotation shafts whose axes intersect and rotatably supporting the mounting part by the at least two rotation shafts, wherein the carrier unit is formed of material that can be sterilized by an application of heat within a temperature range of 120° C.-200° C.; and wherein at least one of the rotation shafts has a rotary damper attached thereon.

2. The tissue-derived biomaterial carrier device of claim 1, wherein a hole is formed in one end face of the mounting part to receive the container, and a barycentric position of the mounting part is located on an opposite side, relative to an opening of the hole, of a location where a rotation shaft of the rotation mechanism supports the mounting part.

3. The tissue-derived biomaterial carrier device of claim 1, further comprising:

a sensor provided inside the carrier case and operable to measure the temperature in the carrier case, wherein the carrier case has an external connection terminal exposed on the exterior wall, and the sensor has a signal cord connecting the sensor and the external connection terminal.

4. The tissue-derived biomaterial carrier device of claim 3, wherein a housing of the carrier case is formed from stainless steel plate, and the sensor and the external connection terminal are resistant to a temperature of at least 200° C.

5. The tissue-derived biomaterial carrier device of claim 3, wherein the temperature control box includes:

a terminal connectable to the external connection terminal exposed on the exterior wall of the carrier case;

a controller operable to perform calculations on the temperature inside the carrier case measured by the sensor; and a power supply unit operable to supply power to the controller and the temperature control unit, and the temperature control unit receives power from the power supply unit when the temperature control box has been attached to the carrier case and controls the temperature inside the carrier case in accordance with a signal from the controller.

6. The tissue-derived biomaterial carrier device of claim 5, wherein the power supply unit includes a battery, and the battery is removable from the temperature control box.

7. The tissue-derived biomaterial carrier device of claim 5, wherein the power supply unit includes a power line for receiving power from an external source.

8. The tissue-derived biomaterial carrier device of claim 1, wherein the temperature control unit includes a heater for heating the tissue-derived biomaterial when the temperature control box has been attached to the carrier case.

9. The tissue-derived biomaterial carrier device of claim 1, wherein the temperature control unit includes a cooling unit for cooling the tissue-derived biomaterial when the temperature control box has been attached to the carrier case.

10. The tissue-derived biomaterial carrier device of claim 9, wherein the tissue-derived biomaterial is film-shaped, and edges thereof bend towards the top of the container when the tissue-derived biomaterial is cooled by the cooling unit.

11. The tissue-derived biomaterial carrier device of claim 9, wherein the temperature control unit includes a Peltier element.

12. A tissue-derived biomaterial carrier device comprising:

a carrier unit comprising a removable top cover that can be hermetically sealed to a lower carrier case, the top cover includes a handle for manual transportation;

a temperature control box is configured to attached and be detachable from an exterior wall of the carrier case to provide one of heat to the carrier case and to remove heat from the carrier case through an exterior wall of the carrier case; and a temperature control unit disposed in the temperature control box and configured to control the temperature in the carrier case, when the temperature control box has been attached to the carrier case, by transferring heat directly through the exterior wall of the carrier case, wherein the carrier unit further comprises:

a sensor;

a mounting part disposed in the carrier case and configured to receive a container storing tissue-derived biomaterial;

a rotation mechanism disposed with respect to an inner wall of the carrier case, the rotation mechanism having at least two rotation shafts whose axes intersect and rotatably supporting the mounting part by the at least two rotation shafts, wherein the carrier unit is formed of material that can be repetitively sterilized by an application of heat within a temperature range of 120° C.-200° C.;

an arm extending into the carrier case from the inner wall thereof; and a damper inserted between the inner wall of the carrier case and the arm to absorb vibration, wherein the mounting part is swingably supported by the rotation mechanism relative to the arm.

13. The tissue-derived biomaterial carrier device of claim 12, further comprising:

the sensor is provided inside the carrier case and operable to measure a temperature in the carrier case, wherein the carrier case has an external connection terminal exposed on the exterior wall, and the sensor has a signal cord connecting the sensor and the external connection terminal.

14. The tissue-derived biomaterial carrier device of claim 13, wherein the sensor, the external connection terminal and the damper are resistant to a temperature of at least 200° C.

15. The tissue-derived biomaterial carrier device of claim 14, wherein the temperature control box includes:

a terminal connectable to the external connection terminal exposed on the exterior wall of the carrier case;

a controller operable to perform calculations on the temperature inside the carrier case measured by the sensor; and a power supply unit operable to supply power to the controller and the temperature control unit, and the temperature control unit receives power from the power supply unit when the temperature control box has been attached to the carrier case and controls the temperature inside the carrier case in accordance with a signal from the controller.

16. A tissue-derived biomaterial carrier device comprising:
a carrier unit comprising a carrier case;
a temperature control box detachable from an exterior wall of the carrier case; and
a temperature control unit disposed in the temperature control box and configured to control the temperature in the carrier case, when the temperature control box has been attached to the carrier case, by transferring heat through the exterior wall of the carrier case, wherein
the carrier unit further comprises:
- a mounting part disposed in the carrier case and configured to receive a container storing tissue-derived biomaterial;
- a rotation mechanism disposed with respect to an inner wall of the carrier case, the rotation mechanism having at least two rotation shafts whose axes intersect and rotatably supporting the mounting part by the at least two rotation shafts, wherein
the carrier unit is formed of material that can be sterilized by an application of heat within a temperature range of 120° C.-200° C.;
an arm extending into the carrier case from the inner wall thereof; and
a damper inserted between the inner wall of the carrier case and the arm, wherein
the mounting part is swingably supported by the rotation mechanism relative to the arm.

17. The tissue-derived biomaterial carrier device of claim 16, wherein
a hole is formed in one end face of the mounting part to receive the container, and
a barycentric position of the mounting part is located on an opposite side, relative to an opening of the hole, of a location where a rotation shaft of the rotation mechanism supports the mounting part.

18. The tissue-derived biomaterial carrier device of claim 16, further comprising:
a sensor provided inside the carrier case and operable to measure the temperature in the carrier case, wherein
the carrier case has an external connection terminal exposed on the exterior wall, and
the sensor has a signal cord connecting the sensor and the external connection terminal.

19. The tissue-derived biomaterial carrier device of claim 18, wherein
the temperature control box includes:
- a terminal connectable to the external connection terminal exposed on the exterior wall of the carrier case;
- a controller operable to perform calculations on the temperature inside the carrier case measured by the sensor; and
- a power supply unit operable to supply power to the controller and the temperature control unit, wherein
the temperature control unit receives power from the power supply unit when the temperature control box has been attached to the carrier case and controls the temperature inside the carrier case in accordance with a signal from the controller.

20. The tissue-derived biomaterial carrier device of claim 16, wherein
the temperature control unit includes one of a heater for heating the tissue-derived biomaterial when the temperature control box has been attached to the carrier case and a controlling unit for cooling the tissue-derived biomaterial when the temperature control box has been attached to the carrier case; and
wherein the temperature control unit includes a Peltier element.

* * * * *